Figure 1:
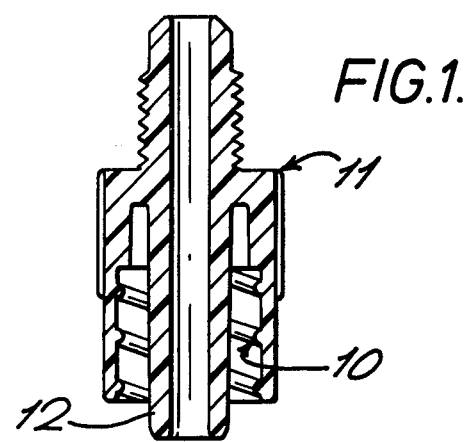

United States Patent [19]

Wallace

[11] 4,360,024

[45] Nov. 23, 1982

[54] CATHETER WITH LIQUID FLOW CONTROL MEANS

[75] Inventor: Henry G. Wallace, Frinton-on-Sea, England

[73] Assignee: H. G. Wallace Limited, Port Lane, Great Britain

[21] Appl. No.: 206,973

[22] Filed: Nov. 14, 1980

Related U.S. Application Data

[63] Continuation of Ser. No. 948,384, Oct. 4, 1978, abandoned.

[30] Foreign Application Priority Data

Oct. 7, 1977 [GB] United Kingdom ............... 41874/77

[51] Int. Cl.³ ............................................ A61M 25/00
[52] U.S. Cl. ..................................... 604/256; 604/283
[58] Field of Search ............. 128/214.4, 348, DIG. 16

[56] References Cited

U.S. PATENT DOCUMENTS

| | | | |
|---|---|---|---|
| 3,454,006 | 7/1969 | Langdon | 128/214.4 |
| 3,856,010 | 12/1974 | Moorehead et al. | 128/214.4 |
| 3,977,400 | 8/1976 | Moorehead | 128/214.4 |
| 4,016,879 | 4/1977 | Mellor | 128/214.4 |
| 4,192,304 | 3/1980 | Millet | 128/214.4 |

Primary Examiner—Dalton L. Truluck
Attorney, Agent, or Firm—Hammond & Littell, Weissenberger & Muserlian

[57] ABSTRACT

A catheter with liquid flow control means having a hub portion and a bore therethrough, where the hub portion is resiliently distortable to close the bore by manual pressure prior to connection of the hub portion to other apparatus, but closure of the bore by manual pressure is prevented after the connection has been made.

1 Claim, 2 Drawing Figures

U.S. Patent     Nov. 23, 1982     4,360,024

CATHETER WITH LIQUID FLOW CONTROL MEANS

This is a continuation of copending application Ser. No. 948,384, filed Oct. 4, 1978, now abandoned.

This invention relates to a catheter incorporating liquid flow control means. The term catheter is used herein to include a cannula or any other tubular surgical device for insertion into the human body.

BACKGROUND OF THE INVENTION

Intravascular catheters, when inserted into a vein or artery, allow blood to flow back through the catheter under its own pressure. In some circumstances this flowback of blood is desirable; however, in others, particularly if uncontrolled, this flow-back and subsequent leaking of blood is inconvenient and even, in some cases, hazardous due to possible contamination of the operator and/or consequent infection of the host or other patients.

A common procedure used to introduce a plastic catheter is to include a sharp hollow needle within the bore of the catheter, which needle acts as a sharp introducer over which the catheter may be advanced into the blood vessel. When the sharp needle is inserted, blood flows rapidly back through the needle but is easily controlled at its proximal end. However, a problem arises when, the catheter having been advanced into the blood vessel, the sharp needle is withdrawn through the bore of the catheter thus allowing blood to flow freely through the catheter until the catheter is connected to other equipment incorporating a control device for the blood flow.

A common practice during this period between withdrawal of the needle and connection to equipment incorporating a blood flow control device is for the operator to palpate the vein into which the catheter is inserted at the skin surface immediately ahead of the catheter tip, thus compressing the vein and preventing or reducing blood flow. However, such a procedure is inconvenient in that it necessitates either multiple operators or a single operator manipulating the withdrawal of the needle and connection of the catheter to other equipment with one hand and, indeed, the procedure is not always feasible. A similar problem arises when a catheter is introduced through the bore of a needle or cannula, for instance a plastic tube, whereby the blood needs to be controlled in the same way.

Various attempts have been made to incorporate blood flow control devices in catheters such as, for example, valves, stopcocks and pieces of flexible tubing. However, such devices have not proved satisfactory. For example, even when open, their construction may result in impedance (resistance) to flow. Furthermore, valves tend to cause clotting of the blood, stopcocks are expensive and bulky, and pieces of flexible tubing are imprecise, cumbersome and add length to the catheter.

In addition, flow control devices with exposed operating means acting to compress an unsupported bore in the hub may result in the hazard of accidental closure of the bore and resultant halt in the administration of a therapeutic substance. Such accidental closure could be produced by strapping of the device, which is a common procedure for retaining an intravenous device in situ on a patient. Accidental pressure could also be applied by any firm surface against which the patient comes in contact. There is, therefore, a need for a catheter having flow control means which mitigate this hazard.

DESCRIPTION OF THE INVENTION

The present invention meets this need by providing a catheter having a hub portion and a bore through said hub portion, said hub portion being resiliently distortable to close said bore by manual pressure, for example, applied adjacent the proximal end of said hub portion prior to connection of said hub portion to other apparatus, but not permitting closure of said bore by manual pressure after such connection.

The term "hub portion" as used herein refers to a coupling, cone, connector (for example a Y-shaped connector as may be used in dialysis, especially hemodialysis), housing or tapered extension of a tube enabling the tube to be connected to another tube, for instance, of a different size.

Preferably, the whole of the catheter hub portion is flexible. Flexibility may, for example, be imparted to the hub portion by the use of a flexible polymer in the construction thereof and by suitable choice of the wall thickness. As will be appreciated, the polymer such as silicone rubber or elastomeric polyurethane, must be suitable for the intended use, that is, suitable not only for prolonged contact with human tissue and particularly blood without adverse effect, but also having appropriate mechanical properties. The hub portion may be incorporated into the catheter either as a separate molding or as part of a one-piece molding including the cannula portion. In the case of a Y-shaped hub portion, at least one of the arms of said hub portion is resiliently distortable to close the bore thereof.

The hub portion is resiliently distortable by a user and preferably comprises portions adapted to be gripped between a finger and thumb of the user to close the bore, for instance, at least one projection or preferably two opposed projections on opposite sides of the hub portion.

Manual pressure exerted on the projection(s) by the user enables the hub portion to be distorted to close the bore when desired. The projection may have an outer surface roughened, for example, by grooves or dimples to aid in providing a firm grip by the user.

Whether or not projections are provided on the hub portion, the region of the hub portion intended to be distorted by the user may be of reduced wall thickness or flanked on one or both sides by portions of reduced wall thickness, for instance by external grooves formed in the hub portion, to facilitate closure of the bore in this region.

In another embodiment, the hub portion is adapted to be bent at a determined position transverse to its longitudinal axis in order to obstruct the bore.

The flexibility and dimensions of the hub portion are so selected that the bore is readily closable by manual pressure prior to connection of the hub portion to another device, such as a transfusion set or the like apparatus, but after the connection is made such closure becomes impossible by the degree of pressure likely to be exerted on the hub portion by strapping or accidental contact with a firm surface while the device is in situ. Connection of the hub portion to the other device will stiffen the proximal end of the hub portion so that it ceases to be readily distortable, and the remainder of the hub portion, if flexible, should be sufficiently rigid to resist closure of the bore by any likely external pressure. Thus, after connection of the hub portion there is no risk of liquid flow through the catheter being unintentionally interrupted.

The proximal end of the hub portion is generally provided with means to engage a mating connection, for instance on a tube carrying a supply of blood or infusion liquid. For example, the bore may be dimensioned to receive a standard Luer or Record connector. Preferably, the proximal end of the hub portion is provided with means, such as lugs, ears, a flange or a threaded portion, to engage the internal thread of a Luer lock or Record lock connector. When so connected, the bore of the hub portion receives the hollow spigot of a male lock connector while the external lugs or the like prevent the connection being accidentally pulled apart. When the whole hub portion is resilient the lugs or the like should preferably be dimensioned to be compressed slightly by the collar portion of the Luer or Record lock, to increase the holding force. The external diameter of said lugs or the like may, for example, be 1–5% greater than the internal diameter of the threaded collar. If normal clearances between the mating portion are allowed, there may be a possibility of the connection being pulled apart by the lugs or the like overriding the threads of the lock connector.

In the embodiment described above the hub portion is the female half of the Luer or Record lock, but less preferably it may be formed as the male portion. The present invention is not restricted to the use of Luer connectors, and the hub portion may be adapted for any other type of pressure-resistant connection. Whether such connection is external, internal or both, it will serve to reduce flexibility of the hub portion at the proximal end and thus prevent inadvertant closure of the bore.

Prior to use, the catheter will ordinarily be packed in a sterile pack so that it can be put into service immediately.

Figure 2:
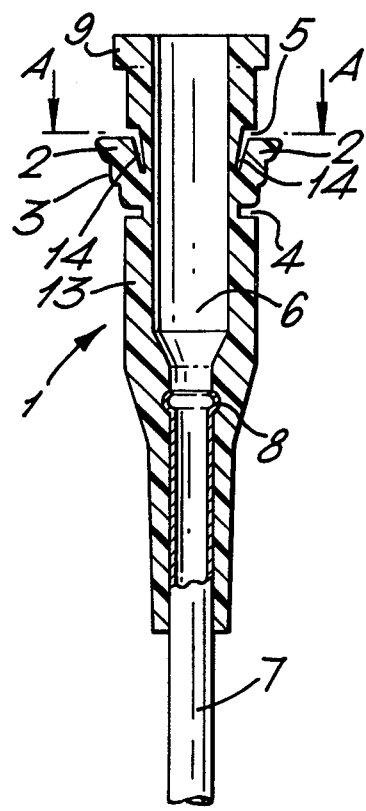
Figure 2:
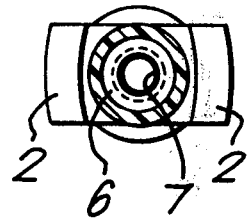

The invention will now be further illustrated by description of a preferred embodiment thereof, with reference to the accompanying diagrammatic drawings wherein:

FIG. 1 is a longitudinal cross-section through a catheter according to the invention, shown adjacent a Luer lock connector; and FIG. 2 is a cross-sectional end view of the catheter of FIG. 1 along line A—A.

Referring to FIG. 1, the catheter comprises a hub portion 1 of elastomeric polyurethane. For clarity this is shown enlarged, its actual length is about 32 mm. The hub portion, near its proximal end, has two projections 2 on opposite sides of the hub portion which have grooved surfaces 3 to afford a better grip to the user's fingers. These projections are flanked by the external circumferential grooves 4 and 5 in the hub portion which increase the flexibility of this region of the hub portion, so that manual pressure on the projections 2, applied for example between a finger and a thumb, is sufficient to close the bore 6 and control back-flow of blood. Slits 14 extend through part of the width of the projections 2, thus increasing flexibility still further.

At its distal end the bore 6 accommodates a cannula 7, made for example of FEP containing a radio-opaque filler. The cannula 7 has a splayed end 8 around which the hub portion has been molded, thus firmly gripping it. In another embodiment the cannular is securely retained by a collar of polystyrene which compresses a tapered nose of the hub portion into firm engagement with the splayed end of the cannula.

At its proximal end the hub portion is provided with a square flange 9 to engage the internal thread 10 of the Luer lock connector 11. The connector is assembled to the catheter by inserting the hollow spigot 12 into the end of bore 6 and twisting the two members while urging them together, thus forcing the thread 10 to engage the four corners of the flange 9 which is oversized by about 2%. The resulting connection is leak-proof and mechanically secure. Moreover, the spigot 12 penetrates into bore 6 up to the proximal end of groove 4, so that if pressure is again applied to the projections 2 the bore 6 is not appreciably distorted and the flow of infusion liquid or the like into a patient is not affected.

The wall thickness of portion 13 is such that it cannot be compressed sufficiently by manual pressure to close the bore in this region.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

What we claim is:

1. In a catheter assembly comprising a flexible catheter tube having an axial bore, a unitary hollow body having a distal end and a proximal end, said catheter tube being inserted into the distal end of said hollow body and in fluid communication with the hollow of the body, the proximal end of said hollow body forming a female infusion fitting, and a male infusion fitting inserted into said female infusion fitting; the improvement which resides in that the hollow body of the catheter assembly consists of a non-collapsible portion extending rearwardly from the distal end and a collapsible portion with memory immediately adjacent to said non-collapsible portion extending to the proximal end, and has a rigid male infusion fitting of the same length as the collapsible portion removably inserted into the collapsible portion, whereby said hollow body becomes non-collapsible over its entire length.

* * * * *

UNITED STATES PATENT AND TRADEMARK OFFICE
CERTIFICATE OF CORRECTION

PATENT NO. : 4,360,024

DATED : November 23, 1982

INVENTOR(S) : HENRY G. WALLACE

It is certified that error appears in the above-identified patent and that said Letters Patent is hereby corrected as shown below:

Title page, [73], the place of assignee's business should read -- Port Lane, Colchester, Great Britain --.

Signed and Sealed this

Tenth Day of May 1983

[SEAL]

*Attest:*

*Attesting Officer*

GERALD J. MOSSINGHOFF

*Commissioner of Patents and Trademarks*